United States Patent [19]
Matsumoto et al.

[11] Patent Number: 5,371,277
[45] Date of Patent: Dec. 6, 1994

[54] CARRIER, CATALYST AND PROCESS FOR PRODUCING UNSATURATED ESTER

[75] Inventors: Kenji Matsumoto, Okayama; Yoshio Fuchigami, Nakajo, both of Japan

[73] Assignee: Kuraray Co., Ltd., Kurashiki, Japan

[21] Appl. No.: 227,700

[22] Filed: Apr. 14, 1994

Related U.S. Application Data

[63] Continuation of Ser. No. 52,292, Apr. 26, 1993, abandoned, which is a continuation of Ser. No. 723,376, Jun. 28, 1991, abandoned.

[30] Foreign Application Priority Data

Jul. 3, 1990 [JP] Japan ................................ 2-177125

[51] Int. Cl.$^5$ ............................................. C07C 69/15
[52] U.S. Cl. ...................................... 560/245; 502/439
[58] Field of Search ......................... 560/245; 502/439

[56] References Cited

U.S. PATENT DOCUMENTS

| | | | |
|---|---|---|---|
| 4,656,157 | 4/1987 | Hofman et al. | 502/439 |
| 4,902,823 | 2/1990 | Wunder et al. | 560/245 |

FOREIGN PATENT DOCUMENTS 10135 6/1973 Japan .
12434 7/1979 Japan .

*Primary Examiner*—Marianne M. Cintins
*Assistant Examiner*—Keith MacMillan
*Attorney, Agent, or Firm*—Oblon, Spivak, McClelland, Maier & Neustadt

[57] ABSTRACT

Provided are a carrier having at least one passing-through channel used for a catalyst for producing unsaturated esters, and a catalyst for producing unsaturated esters comprising an element belonging to Group VIII of the periodic table or compounds thereof carried on said carrier and a process for producing unsaturated esters characterized by the use of said catalyst. The use of the above catalyst markedly increase the space time yield of the obtained unsaturated esters.

4 Claims, 5 Drawing Sheets

CARRIER, CATALYST AND PROCESS FOR PRODUCING UNSATURATED ESTER

This application is a continuation of application Ser. No. 08/052,292, filed on Apr. 26, 1993, now abandoned, which is a continuation of application Ser. No. 07/723,376 filed on Jun. 28, 1991 now abandoned.

BACKGROUND OF THE INVENTION

1. Field of the Invention

The present invention relates to a carrier used for a catalyst for producing unsaturated esters by gas-phase reaction. The invention further relates to a catalyst utilizing said carrier, for producing unsaturated esters by gas-phase reaction, and also to a process for producing unsaturated esters by gas-phase reaction using said catalyst.

2. Description of the Prior Art

There is known a process for producing unsaturated esters which comprises conducting reaction in a gas containing olefin, organic carboxylic acid and oxygen in the presence of a catalyst comprising palladium and/or a palladium compound as essential component, gold and/or a gold compound and an alkali metal compound, which are adsorbed (hereinafter referred to as "carried") on a carrier. Further it is known that higher catalytic activity is obtained by permitting the above noble metals and/or their compounds to be carried concentratively on a specific portion of a carrier. Thus, in the production of unsaturated esters, higher activity is obtained when the catalyst agents are mostly carried on regions close to the surface layer of a carrier (hereinafter this state is referred to as "surface-carrying"). See, for example Japanese Patent Publication Nos. 10135/1973 and 12434/1979.

The carrier used for the catalyst generally has a spherical shape. In recent years there have also been proposed a carrier having a cylindrical shape with rectangular front view and a cylindrical carrier with its both ends being round or hemispherical (Japanese Patent Application Laid-open No. 228940/1989).

It is necessary, for the purpose of producing an unsaturated ester advantageously on industrial scale, to increase the volume of raw material gas comprised of olefin, organic carboxylic acid and oxygen as the catalytic activity increases. (The catalytic activity is hereinafter evaluated by whether high or low the space time yield is.) The first reason to increase the volume of raw material gas is to prevent formation of hot spots on the catalyst, which is caused by increase of catalytic activity because the formation reaction of unsaturated ester is exothermic. The second reason is to maintain the conversion of oxygen within an appropriate range while maintaining the oxygen gas content in the gas below a certain level in order to keep the gas composition outside the range of explosion. Then, an increase in the volume of raw material gas naturally creates a problem of increasing pressure loss in the catalyst layer. This phenomenon of increasing pressure loss has been a barrier against advantageous commercial production of unsaturated esters, in particular when it is attempted to employ a highly active catalyst while using existing equipment. While in the prior art the catalytic activity has been improved by employment of surface-carrying, modification of carrier shape or the like, it has been a large obstacle to the economically advantageous production of unsaturated esters that the increase in the volume of raw material gas to make efficient use of thus increased catalyst activity increases pressure loss in the catalyst layer.

SUMMARY OF THE INVENTION

An object of the present invention is to provide a carrier used for a catalyst for producing unsaturated esters by gas-phase reaction that minimizes the problem mentioned above. Another object of the present invention is to provide a catalyst for the same purpose, and still another object of the present invention is to provide a process for the same purpose.

1: outside diameter (D)
2: inside diameter (d)
3: wall thickness (h)
4: height (l)

DETAILED DESCRIPTION OF THE PREFERRED EMBODIMENTS

As a result of an intensive study to obtain a catalyst with high activity for producing unsaturated esters that can prevent the above-mentioned pressure loss in the catalyst layer from increasing, the inventor has found that this object can be achieved by a catalyst comprising a carrier having at least one passing-through channel, in particular having the shape of a cylinder with a hollow channel therein (hereinafter referred to as "hollow cylinder"), to complete the invention. It has further been found that the use of a catalyst comprising the carrier of the present invention decreases the amount of by-products with high boiling point. The invention is described in detail hereinbelow.

The carrier used in the present invention may assume any shape, as long as it has at least one passing-through channel, and its examples include a hollow cylinder, a ring, honeycombs having one or at least 2 passing-through channels, a block having a cross-shaped passing-through channel and the like, their examples being shown in FIGS. 1 through 11.

Figure 1:
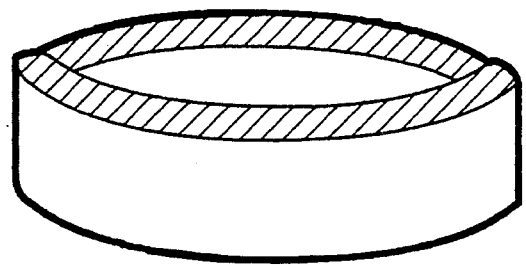
FIG. 1 is a schematic view of a carrier with one passing-through channel.
Figure 2:
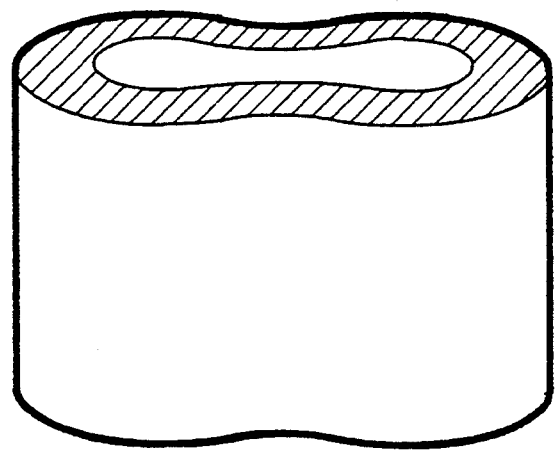
FIG. 2 is a schematic view of another carrier with one passing-through channel.
Figure 3:
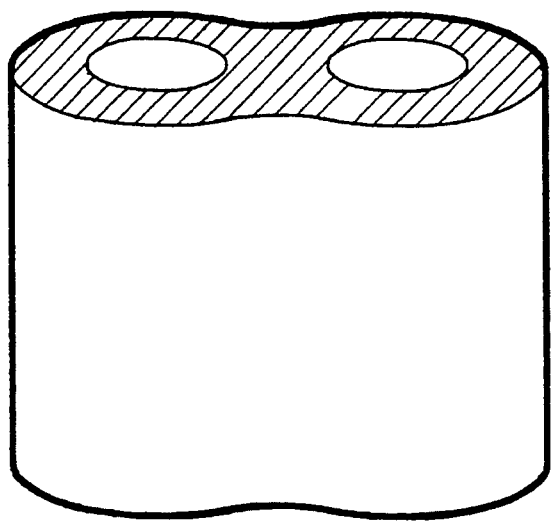
FIG. 3 is a schematic view of a carrier with 2 passing-through channels.
Figure 4:
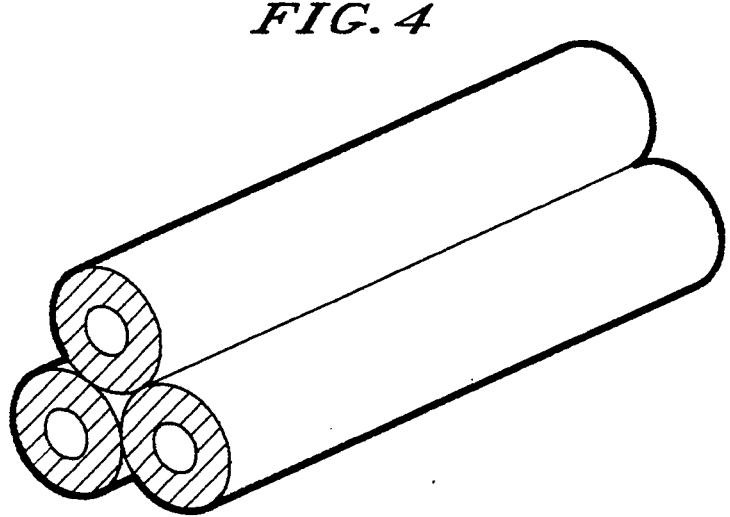
FIG. 4 is a schematic view of a carrier with 3 passing-through channels.
Figure 5:
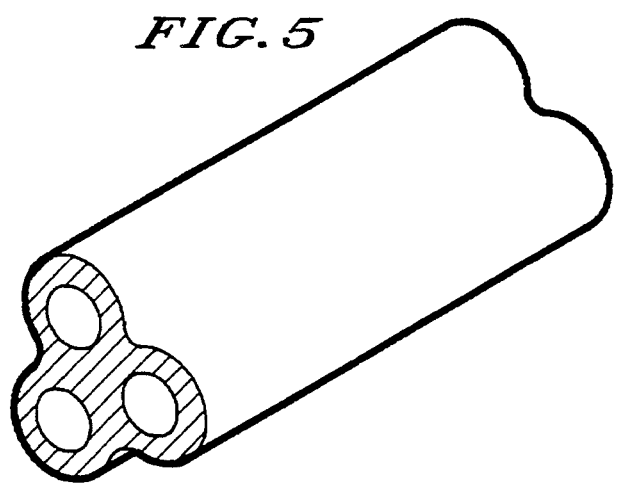
FIG. 5 is a schematic view of another carrier with 3 passing-through channels.
Figure 6:
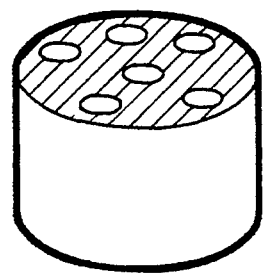
FIG. 6 is a schematic view of a carrier with a multiplicity of passing-through channels.
Figure 7:
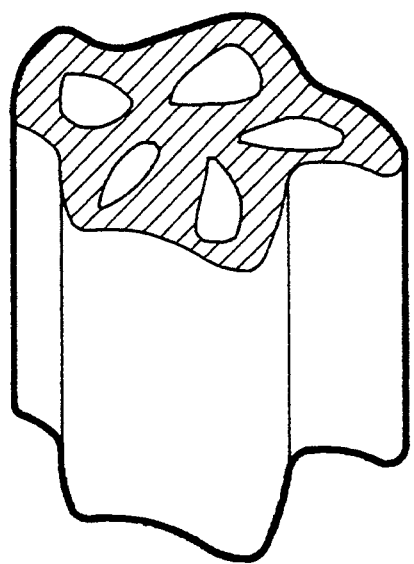
FIG. 7 is a schematic view of another carrier with a multiplicity of passing-through channels.
Figure 8:
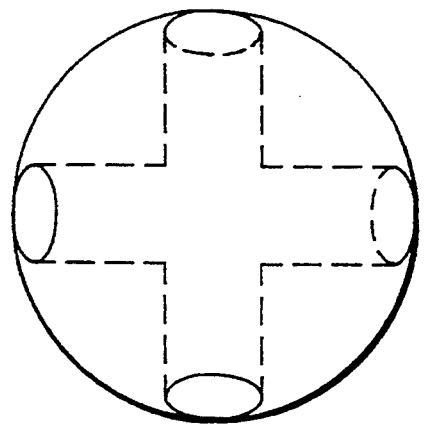
FIG. 8 is a schematic view of a carrier with a cross-shaped passing-through channel.
Figure 9:
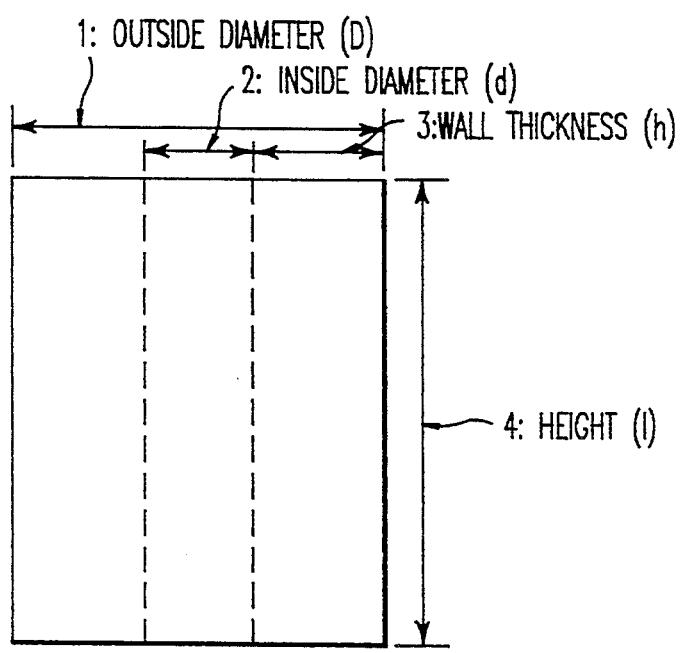
FIGS. 9 is a front view of a carrier having the shape of hollow cylinder.
Figure 10:
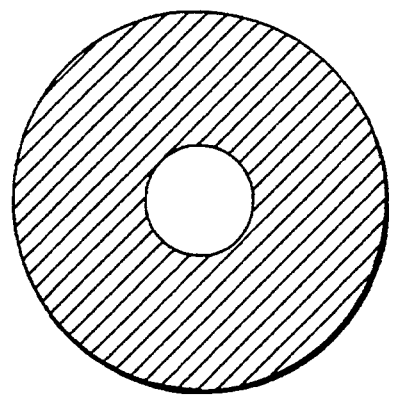
FIG. 10 is a top view of the carrier shown in FIG. 9.
Figure 11:
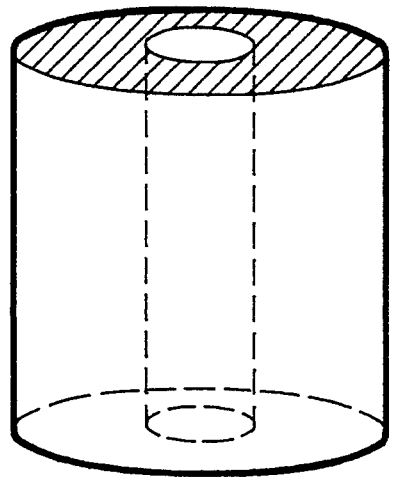
FIG. 11 is a schematic view of the carrier shown in FIGS. 9 and 10.

FIGS. 1 and 2 show carriers with one passing-through channel, FIG. 3 shows a carrier with 2 passing-through channels and FIGS. 4 and 5 show those with 3 passing-through channels. FIGS. 6 and 7 show carriers with a multiplicity of passing-through channels and FIG. 8 shows one with a cross-shaped passing-through channel. FIGS. 9 through 11 show examples of a carrier having the shape of hollow cylinder, wherein D, d, h and l represent outside diameter, inside diameter, i.e. diameter of hollow space, wall thickness, i.e. the width of solid part in the cross section and height, respectively. In this case the wall thickness (h) and the height (l) need not be uniform and wall shapes having projections and/or concaves are, naturally, also included in the scope of the present invention. It is preferred for the size of this hollow cylinder that the outside diameter (D), inside diameter (d), wall thickness (h) and height (l) be within ranges of 3 to 10 mm, at least 1 mm, not more than 3 mm and 2 to 10 mm, respectively, but the sizes principally satisfying these conditions may also be suitably used. If the outside diameter (D) and the height (l) exceed these ranges, a multiplicity of such carrier pellets will be difficult to appropriately pack in a reaction tube of a fixed bed reactor. On the other hand, if these dimensions are smaller than the above ranges, the pressure loss will be too large to meet the object of the present invention. The wall thickness (h) is preferably as thin as possible within the range that permits the strength of the carrier to be industrially usable. If the inside diameter (d) is less than 1 mm, the pressure loss will increase, thereby lowering the effect of the present invention.

The carrier may be of any material, but is preferably made of silica and/or alumina.

Specific surface area, pore volume and pore diameter are known property items for carriers suited for catalysts for the production of unsaturated esters. In this invention, the carrier preferably has a specific surface area as measured by BET method of 50 to 200 m$^2$/g, and is formed of micropores having a pore volume as measured by mercury porosimetry of 0.3 to 1.0 ml/g, of which at least 50% have a diameter of 40 to 400 angstroms.

The carrier may be formed by any process including, for example, molding and pressing.

The catalyst of the present invention is now described.

The catalyst of the present invention comprises an active catalyst agent of at least one element selected from Group VIII of the periodic table or compounds thereof carried on the above-described carrier having at least one passing-through channel. It is preferred that the catalyst of the present invention comprises, besides the active catalyst agent, promoter (I) which comprises at least one element selected from Group Ib of the periodic table or compounds thereof. It is still more preferred that the catalyst of the present invention further comprises, besides the active catalyst agent and the promoter (I), an active agent component (hereinafter referred to as "promoter (II)") which is an alkali metal compound comprising an element belonging to Group Ia of the periodic table.

Preferred among the above element selected from Group VIII of the periodic table and the element selected from Group Ib of the periodic table are palladium and gold, respectively. All the salts and complexes of palladium and gold can be used, among which preferably selected are those being soluble in water or solvents suited for catalyst and, when to be used in the form of metal in a catalyst, being readily reducible into metal form. Preferred among these are carboxylates, and more particularly, salts or sodium salts of chlorides of aliphatic monocarboxylic acids having 2 to 5 carbon atoms, such as acetates, propionates and butyrates. Particularly preferred among these palladium compounds are palladium acetate and palladium sodium chloride in view of solubility and availability. From the same reason, prefer-red gold compound is chloroauric acid (tetrachloroauric acid).

Palladium or its compound is contained in the catalyst in an amount as palladium of 1 to 20 g/l, preferably 2 to 10 g/l; and gold or its compound is contained in an amount as gold of 0.1 to 10 g/l, preferably 0.2 to 5 g/l.

The catalyst of the present invention preferably comprises an alkali metal compound as promoter (II). Examples of preferred alkali metal compounds are alkali carboxylates such as potassium acetate, sodium acetate, lithium acetate and sodium propionate. Also usable are hydoxides, oxides and carbonates of alkali metals that convert to carboxylates under the reaction conditions. The promoter (II) is generally added in an amount of 5 to 80 g/l, preferably 10 to 50 g/l.

The combination of palladium, gold and an alkali metal compound is particularly preferred among combinations of the above active catalyst agent, promoter (I) and promoter (II). In this case, it is preferred that palladium and gold be contained in the catalyst as metals or their compounds, and the alkali metal compound be contained as carboxylate of an alkali metal, particularly potassium.

The active catalyst agent and the promoter (I) (hereinafter the two in combination or, only the former when the latter is not used, are referred to as "carried substance") can be carried on a carrier uniformly (hereinafter this state is referred to as "uniform carrying") by for example immersing the carrier in a solution comprising the carried substance and then, if necessary, reducing it. Or, the carried substance can be surface-carried by, for example, a process which comprises immersing the carrier in a solution containing a small portion of the carried substance, reducing it if necessary, re-immersing the carrier in a solution containing the rest of the carried substance, a process which comprises spraying a solution containing the carried substance onto the carrier, followed by the reduction thereof, or like processes.

In impregnating a carrier with a carried substance, it is advantageous to immerse the carrier in a solution containing the carried substance and having a volume equal to the integrated pore volume of the carrier and then mix the solution sufficiently. By this method the carried substance is uniformly carried on all the particles of the carrier material. Agitation is an advantageous method for sufficient mixing. The immersion and the mixing can be conducted simultaneously in, for example, a rotating drum or a drum drier.

In conducting reduction of a palladium compound or a gold compound, generally employed is a process which comprises immersing the catalyst having completed impregnation of the carried substance in a solution containing a reducing agent and allowing the mixture to stand still for a prescribed time. Hydrazine.hydrate is a suitable reducing agent in view of availability. There may also be employed a process which comprises diluting a gas such as hydrogen, methanol, formaldehyde, ethylene or propylene with an inert gas such as nitrogen or carbon dioxide, and conduct reduc-tion at an elevated temperature of 50° to 100° C.

The promoter (II) can be carried on a carrier in the same manner as in the case of impregnation with the carried substance.

The activity of a catalyst is evaluated by for example the measurement of surface area of carried metal (hereinafter referred to as "MSA") by determining the CO absorbability. See HANDBOOK OF CATALYST EXPERIMENT, an extra number of "CATALYST COURSE" edited by Japan Catalyst Association, 1986, pages 183-185. The catalyst comprising the carrier of the present invention having at least one passing-through channel gives clearly higher MSA than those of catalysts comprising a round or cylindrical carrier having the same outside shape and no hollow channels.

The catalyst of the present invention exhibits particularly marked catalytic activity when the carried substance is surface-carried, especially on the vicinity of the surface layer of the outside surface and that of the surface of the inner wall of the passing-through channel, i.e. all surface layers of all the surfaces of the carrier.

The process for producing unsaturated esters according to the present invention is described next.

The process for producing unsaturated esters of the present invention comprises using a catalyst comprising the above-described carrier having at least one passing-through channel with an carried substance and, preferably, promoter (II) carried thereon and conducting reaction in the gas phase containing an olefin, an organic carboxylic acid and oxygen at 100° to 220° C., preferably 120° to 200° C. and under a pressure of 1 to 25 atmospheres, preferably 1 to 15 atmospheres, through a fixed bed catalyst reactor. Here components remaining unreacted can be recycled.

There is no specifical limit as to the space velocity used, but it is preferably in a range of from 2000 to 5000 hr$^{-1}$; and in the present invention stable production operation is possible with the space velocity of not less than 3000 hr$^{-1}$.

Examples of the olefin are ethylene, propylene, butene, pentene, hexene and the like, among which ethylene and propylene are particularly preferred.

Examples of the organic carboxylic acid are formic acid, acetic acid, propionic acid and the like, among which acetic acid is particularly preferred.

The gas phase used for the reaction and comprising an olefin, an organic carboxylic acid and oxygen should maintain the oxygen concentration outside the explosion limit under the applied conditions.

It is advantageous to dilute the gas with an inert gas such as nitrogen or carbon dioxide under a prescribed condition. Of the two, carbon dioxide is more suited for the dilution in a circulating system, since carbon dioxide forms in a small amount during reaction. A part of the olefin used is consumed in combustion reaction, i.e. reaction with oxygen. This combustion reaction is accelerated as the temperature is elevated, and hence it is preferred to suppress the elevation of gas temperature on the catalyst as low as possible.

While several byproducts other than carbon dioxide have been observed, generation of byproducts other than the desired product and having a low or high boiling point should be suppressed to as low an extent as possible, since they are difficult to separate. Byproducts, particularly those having a high boiling point, contain compounds having a structure comprising the desired product with acetic acid added thereto. From this fact, it is considered that secondary addition reaction proceeds as the desired reaction proceeds. It is preferred for the purpose of suppressing the secondary addition reaction not to prolong the time of contact with catalyst longer than necessary.

The process for producing unsaturated esters of the present invention is suitably used for the production of vinyl esters such as vinyl formate, vinyl acetate and vinyl propionate and allyl esters such as allyl formate, allyl acetate and allyl propionate, among which particularly suitable are the production of vinyl acetate and allyl acetate.

The catalyst comprising a carrier having at least one passing-through channel used in the present invention has been found to overcome all the unsatisfactory points associated with the prior art.

Thus, its advantages over conventional carriers of spherical or cylindrical shape with no channels are as follows:

① can increase space time yield;
② can increase the space velocity of raw material gas, thanks to small pressure loss in the catalyst layer;
③ can keep high selectivity to the desired product even at high space time yield, since the temperature elevation in the catalyst layer is suppressed by increasing the space velocity; and
④ can suppress formation of byproducts caused by secondary addition reaction, since the time of contact with the catalyst is maintained as short as possible by increasing the space velocity even at high space time yield.

As is apparent from the following Examples, the use of a catalyst comprising a carried substance and, preferably, promoter (II) carried on a carrier having at least one passing-through channel, particularly one having the shape of hollow cylinder, significantly increases the space time yield of the resulting unsaturated esters. Thanks to small pressure loss in the catalyst layer, employment of reaction conditions including increased space velocity is possible, whereby the space time yield is significantly increased without lowering the selectivity to the desired product. Furthermore, formation of byproducts is suppressed.

The advantages of the process of the present invention are as follows: By using the catalyst of the present invention, when an apparatus for producing unsaturated esters is newly constructed, the volume of the reactor can be decreased, thereby significantly reducing the equipment cost; or, when an existing apparatus is used, the production can substantially be increased without increasing the capacity of the existing reaction vessel, thereby saving the expense for expanding the apparatus which would otherwise be required for increasing the production. Furthermore, by using this catalyst, significantly higher selectivity to the desired product can be attained in the production than in the case of using conventional catalyst and with the same space time yield, thereby greatly cutting down the amount of olefin consumed.

EXAMPLES

Hereinbelow the present invention is described in more detail with reference to Examples. In the Examples "%" means "% by weight" unless otherwise specified.

Example 1

A carrier formed principally of silica, having a hollow cylindrical shape and having the below-described dimensions was used.

Dimensions:

| | |
|---|---|
| outside diameter (D) | 5.1 mm |
| inside diameter (d) | 2.0 mm |
| wall thickness (h) | 1.55 mm |
| height (l) | 4.1 mm |

Catalysts were prepared using this carrier as follows.

Uniformly-carried Catalyst

The above carrier was impregnated with an aqueous solution containing palladium sodium chloride ($PdCl_2 \cdot 2NaCl$) as a palladium salt and tetrachloroaurate as a gold salt, and then the noble metal salts were reduced with a reducing agent of hydrazine.hydrate which is capable of reducing palladium salts and gold salts to the metals. Thereafter the carrier with the metals were washed with water, then impregnated again with potassium acetate (KOAc) as an alkali metal acetate, and dried.

The amounts of the noble metals carried were adjusted to a Pd content of 5.0 g/l and an Au content of 0.5 g/l, and KOAc was adjusted to a content of 20 g/l.

Surface-carried Catalyst

In the same manner as in the case of preparing uniformly-carried catalyst, 0.2 g/l of Pd and 0.09 g/l of Au were firstly carried, and similar procedure was repeated to permit 5.0 g/l of Pd and 0.5 g/l of Au to be finally carried. Further 20 g/l of KOAc was carried. The catalyst thus prepared was tested by X-ray microanalysis to show that at least 95% of Pd and Au extended less than 0.5 mm from the surface. The MSA was 90 $m^2/g$ for the surface-carried catalyst.

Two sets of a multiplicity of the thus prepared uniformly-carried catalyst and surface-carried catalyst were each packed in a reaction tube equipped with jacket and having an inside diameter and a length of 25 mm and 6 m respectively. A gas containing 72% by volume of ethylene, 8% by volume of oxygen and 20% by volume of acetic acid was passed through the catalyst layer thus prepared at an oil temperature of the cooling jacket side of 160° C. and under a pressure of 10 atm and at a space velocity (hereinafter referred to as "SV") of 2000 $hr^{-1}$, to permit reaction to take place. The space time yield of vinyl acetate formed, selectivity to vinyl acetate based on ethylene amount and ratio of high-boiling-point byproducts formed are shown in Table 1.

The amount of high-boiling-point byproducts formed is shown in terms of an index based on 100 of the amount formed per space time yield in the case of surface-carried catalyst. This applies also to the cases of Examples and Comparative Examples that follow. The pressure loss was 0.2 $kg/cm^2$ for both cases.

The amount of high-boiling-point byproducts formed was compared by using the ratio of the area of gas chromatographical peaks, obtained by the below-described gas chromatography, which were thought to be from those having a boiling point of at least 130° C.

Apparatus: GC-6A(1), made by Shimadzu Corporation

Column: inside diameter 3 mm, length 3 m, glass

Packings: FAL-M 25%/carrier Chromosolve W-AW, DMCS, $H_3PO_4$ 80 to 100 mesh

Measuring condition: column temperature 95° C.

Detector: FID 210° C.

Carrier gas: $N_2$ 30 ml/min

Comparative Example 1

Example 1 was repeated except for using a spherical carrier having the same composition as that of Example 1, to effect reaction. The results are shown in Table 1. The space time yield was lower and the pressure loss was larger than in the case of Example 1. The MSA was 70 $g/m^2$ for surface-carried catalyst.

Comparative Example 2

Comparative Example 1 was repeated except for using a cylindrical carrier with no channels having an outside diameter (D) of 5.1 mm and a height (l) of 4.1 mm, to effect reaction. The results are shown in Table 1. The MSA was 81 $m^2/g$ for surface-carried catalyst.

Comparative Example 3

Comparative Example 1 was repeated except for using a cylindrical carrier having semispherical ends, to effect reaction. The results are shown in Table 1.

TABLE 1

| | Example 1 | | Comp. Ex. 1 | | Comp. Ex. 2 | | Comp. Ex. 3 | |
|---|---|---|---|---|---|---|---|---|
| | Hollow cylinder (SV 2000 $hr^{-1}$) | | Sphere (SV 2000 $hr^{-1}$) | | Solid cylinder (SV 2000 $hr^{-1}$) | | Cylinder with semi-spherical ends (SV 2000 $hr^{-1}$) | |
| Carrying condition | Uniform | Surface | Uniform | Surface | Uniform | Surface | Uniform | Surface |
| Space time yield (g/l · hr) | 250 | 400 | 180 | 300 | 200 | 330 | 210 | 340 |
| Selectivity (%) | 94 | 92 | 95 | 93 | 94 | 93 | 95 | 93 |
| High-boiling point byproducts (index) | 100 | 100 | 100 | 100 | 100 | 100 | 100 | 100 |
| Pressure loss (kg/$cm^2$) | 0.20 | 0.20 | 0.26 | 0.26 | 0.26 | 0.26 | 0.28 | 0.28 |
| MSA ($m^2/g$) | — | 90 | — | 70 | — | 81 | — | — |

Example 2

Synthesis reaction was effected using the same catalyst and apparatus as used in Example 1 except that the space velocity of the raw material gas was 3000 $hr^{-1}$, i.e. 1.5 times that in the case of Example 1. The results are shown in Table 2.

Both the space time yield and the selectivity were high, with small increase in pressure loss and small amount of byproducts formed.

Comparative Examples 4 through 6

Comparative Examples 1 through 3 were repeated except that the space velocity of the raw material gas was changed to 3000 $hr^{-1}$, i.e. 1.5 times that used in these Comparative Examples, to be Comparative Examples 4 through 6, respectively. The results are shown in Table 2.

It was found that, in Comparative Examples 4 through 6 where the space velocity was 3000 hr$^{-1}$, the pressure loss was larger than in Example 2, which is not preferred from the viewpoint of commercial production for vinyl acetate.

TABLE 2

|  | Example 2 | | Comp. Ex. 4 | | Comp. Ex. 5 | | Comp. Ex. 6 | |
| --- | --- | --- | --- | --- | --- | --- | --- | --- |
| Carrier | Hollow cylinder (SV 3000 hr$^{-1}$) | | Sphere (SV 3000 hr$^{-1}$) | | Solid cylinder (SV 3000 hr$^{-1}$) | | Cylinder with semi-spherical ends (SV 3000 hr$^{-1}$) | |
| Carrying condition | Uniform | Surface | Uniform | Surface | Uniform | Surface | Uniform | Surface |
| Space time yield (g/l · hr) | 300 | 440 | — | — | — | — | — | — |
| Selectivity (%) | 92 | 93 | — | — | — | — | — | — |
| High-boiling point byproducts (index) | 73 | 80 | — | — | — | — | — | — |
| Pressure loss (kg/cm$^2$) | 0.45 | 0.45 | 0.60 | 0.60 | 0.60 | 0.60 | 0.64 | 0.64 |
| MSA (m$^2$/g) | — | 90 | — | 70 | — | 81 | — | — |

Example 3

Example 1 was repeated except for using propylene as an olefin instead of ethylene, changing the space velocity, pressure of raw material gas and the temperature of the cooling jacket side to 2,000 hr$^{-1}$, 5 atm and 140° C., respectively, using a catalyst comprising no gold and changing the raw material gas composition as follows.

Propylene: 12% by volume, nitrogen: 72% by volume

Oxygen: 7% by volume, acetic acid: 9% by volume

The space time yield of the resulting allyl acetate was 190 g/l.hr and the selectivity was 97%.

What is claimed is:

1. A process for producing an unsaturated ester, comprising:

reacting an olefin, an organic carboxylic acid and oxygen in the gas phase at a space velocity of 2000 to 5000 hr$^{-1}$ in the presence of a catalyst comprising a carrier having the shape of a hollow cylinder and a palladium or a compound thereof in an amount of 1 to 20 g/l, as palladium, and gold or a compound thereof in an amount of 0.1 to 10 g/l, as gold, deposited thereon such that at least 95% of the deposited metals or compounds thereof are deposited to a depth of within 0.5 mm from the surface of the carrier.

2. The process of claim 1, wherein said unsaturated ester is vinyl acetate or allyl acetate.

3. The process of claim 1, wherein the catalyst further comprises potassium acetate or sodium acetate as a promoter.

4. The process of claim 1, wherein said hollow cylinder has an outside diameter of 3 to 10 mm, an inside diameter of at least 1 mm, a wall thickness of not more than 3 mm and a height of 2 to 10 mm.

* * * * *